United States Patent [19]

Pinchuk

[11] Patent Number: 4,759,757
[45] Date of Patent: Jul. 26, 1988

[54] CARDIOVASCULAR GRAFT AND METHOD OF FORMING SAME

[75] Inventor: Leonard Pinchuk, Miami, Fla.
[73] Assignee: Corvita Corporation, Miami, Fla.
[21] Appl. No.: 6,101
[22] Filed: Jan. 23, 1987

Related U.S. Application Data

[62] Division of Ser. No. 601,676, Apr. 18, 1984, Pat. No. 4,657,544.

[51] Int. Cl.$^4$ ............................ A61F 2/06; B29C 27/60
[52] U.S. Cl. ............................................. 623/1; 264/41
[58] Field of Search ........................... 623/1, 12; 264/41

[56] References Cited

U.S. PATENT DOCUMENTS

| | | | |
|---|---|---|---|
| 4,319,363 | 3/1982 | Ketharanathan | 623/1 |
| 4,334,327 | 6/1982 | Lyman et al. | 623/12 |
| 4,355,426 | 10/1982 | MacGregor | 623/1 |

FOREIGN PATENT DOCUMENTS 1552388  9/1979  United Kingdom ..................... 623/1

*Primary Examiner*—Ronald L. Frinks
*Attorney, Agent, or Firm*—Henry W. Collins; Thomas R. Vigil

[57] ABSTRACT

The method for forming a biocompatible polymer graft particularly adapted for cardiovascular use comprises the steps of: choosing a suitable, non-solvent, two component, hydrophobic biocompatible polymer system from which the graft may be formed; choosing a suitable water soluble inorganic salt to be compounded with the biocompatible polymer system; grinding the salt crystals and passing same through a sieve having a predetermined mesh size; drying the salt crystals; compounding the salt crystals with the biocompatible polymer system; forming a tube from said compounded salt and polymer system by reaction injection or cast molding; and leaching the salt crystals from the formed tube with water, said leaching of said salt crystals providing a tube with a network of interconnecting cells formed in the area from which the salt crystals have been leached.

Further, according to the present invention, there is also provided a graft particularly adapted for cardiovascular use, said graft comprising a tube which has been reaction injection molded, cast molded, or extruded from a non-solvent, two component hydrophobic biocompatible polymer system and which has a honeycomb of interconnecting cells throughout the thickness of its wall formed by the leaching of a compounded inorganic salt therefrom.

14 Claims, 1 Drawing Sheet

CARDIOVASCULAR GRAFT AND METHOD OF FORMING SAME

This is a division of application Ser. No. 601,676, filed Apr. 18, 1984, now U.S. Pat. No. 4,657,544.

BACKGROUND OF THE INVENTION

1. Field of the Invention

The present invention relates to a cardiovascular graft and a method of forming same. More particularly, the invention relates to a cardiovascular graft fabricated of a porous, biocompatible polymer system which provides for cellular ingrowth and/or increased flexibility. The method of forming the graft utilizes a non-solvent, two component, hydrophobic polymer system.

2. Description of the Prior Art

Heretofore various porous graft structures and methods of forming same have been proposed.

Two such graft structures and methods for their formation are disclosed in the following U.S. Patents:

| U.S. Pat. No. | PATENTEE |
|---|---|
| 4,334,327 | Lyman |
| 4,355,426 | MacGregor |

The Lyman U.S. Pat. No. 4,334,327 discloses a flexible ureteral prosthesis (graft) fabricated from copolyurethane materials. The prosthesis includes an elongate duct having a lumen whose interior surface is ultrasmooth to impede incrustation. An external cuff, formed of a foam-like material, is formed around a portion of the elongate duct. The cuff has at least 40% void space therein which provides a proper density for receiving sutures to enable fixation of the cuff by suturing to appropriate muscular tissue. The inner diameter of the prosthesis must be conformed to the outer diameter of the ureter of the recipient. Further, the prosthesis is provided with a one-way valve to prevent backflow of urine.

The process of formation of the prosthesis involves selecting a tubular mandrel having a highly polished surface and an outer diameter corresponding to a desired inner diameter for the prosthesis. One end of the mandrel is configured to conform to a cavity shape which is of acceptable size for forming the body of the one-way valve.

The next step in this process involves applying a fluid layer of block copolymer to the mandrel. The block copolymers found particularly suitable as ureter replacement materials include copolyurethanes, copolyether-urethanes and/or copolyether-urethane-ureas. With the mandrel suitably coated, the copolymer layer is solidified to fix its shape into conformance with the mandrel surface. Mold blocks are than secured around terminal segments at each end of the coated mandrel to form boundaries for the formation of an exterior cuff. These blocks have an opening centrally disposed therein corresponding to an approximate diameter of the coated mandrel to facilitate mounting of the mandrel within the respective mold blocks. The cuff is then formed by permanently affixing a material whose final state develops a foam-like composition over the coated mandrel between the mold blocks. Once the cuff is formed and appropriately configured to facilitate suturing to fascia within the patient, the mold blocks are removed and the mandrel withdrawn. The foam like end product structure may be fabricated by admixing powdered inorganic salt to a solution of approximately 12% to 17% (w) block copolymer or may utilize a fluid transfer method for establishing the voids throughout the cuff material.

The MacGregor U.S. Pat. No. 4,355,426 discloses a cardiovascular prosthetic device comprising a porous surface and a network of interconnected interstitial pores below the surface of the device in fluid flow communication with the surface pores.

Several other devices are disclosed which fall broadly into two classes, rigid items and flexible polymeric items.

The flexible porous polymeric grafts are formed from a segmented polyurethane and more preferably a segmented hydrophilic polyurethane. The graft may be provided with a porous surface and subsurface network on a coherent substrate or may be formed as a wholly porous structure.

Various specific structural embodiments of flexible graft are dependent upon the function the graft is to serve, as disclosed in the MacGregor patent.

Further, MacGregor proposes several different procedures for forming the various graft structures defined, all of which require the use of a polymer resin and a solvent.

As described above, the prior methodology of formation of graft structures has involved the mixing of water soluble inorganic salts into polymer-solvent systems and then forming a graft of a desired but limited thickness by one of many procedures available. The resulting polymer network is then cured and leached of salt by soaking in an aqueous solution.

Also, foaming agents and blowing agents have been used to produce "pseudo-porous grafts", i.e., to produce a closed pore cellular structure to the graft. The pore sizes are often irregular and difficult to control and can be larger than the 200 micron maximum size recommended for tissue ingrowth. Further, the by-products of the foaming reaction can be physiologically damaging.

Additionally, use of mandrel dipping methods results in grafts which are limited to simple, thin-walled grafting material with reproducibility and uniformity being unattainable.

As will be described in greater detail hereinafter, the graft and method of the present invention have a number of advantages over the prior art grafts and methods, such advantages including a simple method of formation using a nonsolvent polymer system, ease of reproducibility of the exact graft structure, uniformity of the porous network within the graft while allowing for variable porosity and variable wall thickness of the graft, and the use of hydrophobic materials in the production of the graft.

SUMMARY OF THE INVENTION

According to the present invention, there is provided a method for forming a biocompatible polymer graft particularly adapted for cardiovascular use, said method comprising the steps of: choosing a suitable, non-solvent, two component, hydrophobic biocompatible polymer system from which the graft may be formed; choosing suitable water soluble inorganic salt crystals to be compounded with the biocompatible polymer system; grinding the salt crystals and passing same through a sieve having a predetermined mesh size; drying the salt crystals; compounding the salt crystals with the biocompatible polymer system; forming a tube from said compounded salt and polymer system by reaction injection or cast molding; and leaching the salt crystals from the formed tube with water, said leaching of said salt crystals providing a tube with a network of interconnecting cells formed in the area from which the salt crystals have been leached.

DESCRIPTION OF THE PREFERRED EMBODIMENT

Figure 1:
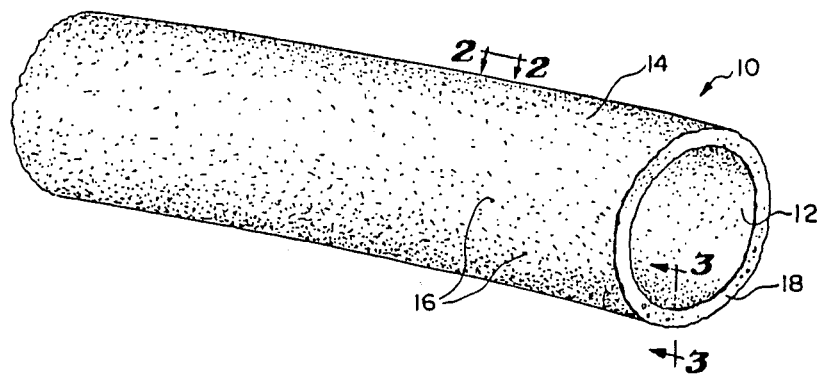
FIG. 1 is a perspective view of the cardiovascular graft of the present invention.

Referring now to the drawings in greater detail, there is illustrated in FIG. 1 a graft 10, particularly adapted for cardiovascular use. As illustrated, the graft 10 has a tubular configuration within an inner surface 12 and an outer surface 14 and is formed of a porous biocompatible polymer material with the surface 12 and 14 having cells or pores 16 therein.

Figure 2:
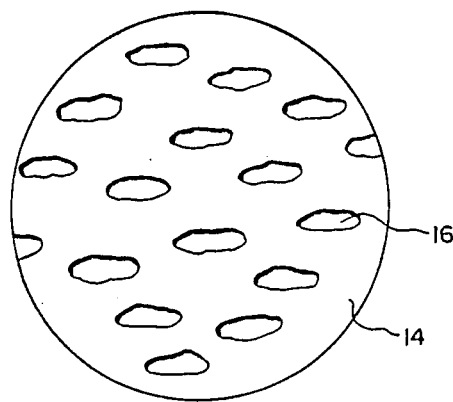
FIG. 2 is a magnified view in section of the outer surface of a section of the graft taken along line 2—2 of FIG. 1 and shows the porous nature of the surface of the graft.

Referring now to FIG. 2, there is illustrated therein a magnified view of the outer surface 14 of the graft 10 of the present invention and is taken along line 2—2 of FIG. 1.

This magnified view of the outer surface 14 shows that the pores 16 are all substantially uniform. However, the diameter of these pores 16 may vary from graft to graft as dictated by the location at which the graft 10 is to be used within the cardiovascular system. For example, if the graft 10 were to be positioned in a popliteal artery, the pore diameter would be larger than the pore diameter of a graft 10 that would be used in say, an area such as the hand. Regardless of the site of use of the graft 10, the diameter of the pores 16 within each particular graft will remain constant and uniform.

It has been found through empirical studies that the diameter of these pores or cells 16 may range from 1 micron to 200 microns and still allow for fixation of the graft to tissue underlying the area in which the graft 10 is to be positioned. In this respect, the diameter range has been found useful in that a suture placed through the graft 10 will be easily fed through the graft material at one range extreme which at the other range extreme, the porosity is not great enough to allow for tearing of the graft material when a suture is passed through same.

Figure 3:
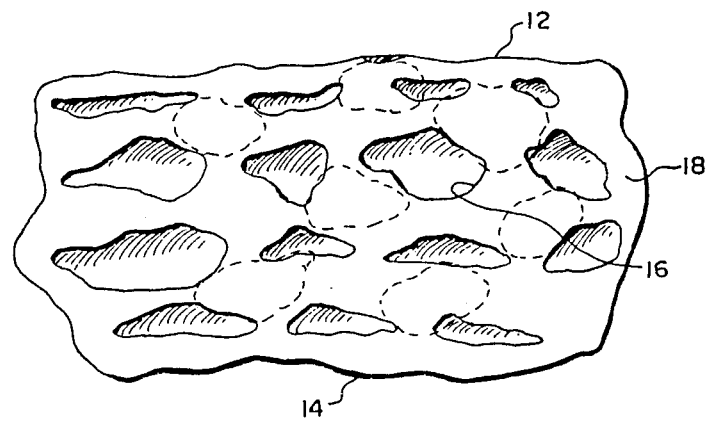
FIG. 3 is an enlarged cross-sectional view of the graft wall, is taken along line 3—3 of FIG. 1 and shows the honeycomb configuration of the pores throughout the thickness of the graft wall.

Referring now to FIG. 3, there is illustrated therein a cross-sectional microscopic view through the wall 18 of the graft 10 of the present invention which is taken along line 3—3 of FIG. 1. In this view is illustrated the honeycomb arrangement of the cells or pores 16. In this respect, by forming the graft 10 by the method of the present invention, the cells or pores 16 within the graft are formed so that they interconnect throughout the wall thickness to form a porous network through the wall 18 to the graft 10. This honeycomb network arrangement in a porous biocompatible polymer facilitates diffusion of nutrient-containing tissue into the interconnecting cells 16. Further, with a maximum pore size of 200 microns, cellular ingrowth is promoted to form a substrate of connective tissue on which a pseudointima may form. Further, the constant diffusion of nutrient material through the graft wall 18 afforded by he honeycomb network prevents tissue necrosis along the inner surface of the cardiovascular graft 10 and prevents sloughing off of the pseudointima with an end result of an encapsulated cardiovascular graft 10 with tissue filling the cells 16 and a smooth endothelial surface forms over the inner surface 12 of the graft 10 over which the blood will flow.

Turning now to the method for forming the graft 10, it is first to be noted that the biocompatible polymer system from which the graft is manufactured is a two component polymer system including as polyurethane, silicone and polytetrafluorethylene and a curing agent. Also, other hydrophobic polymer systems may be utilized and the choice of materials should not be confined to these three polymers.

In such a two component polymer system, the first component is a resin, such as a silicone resin, and the second component is a curing agent/catalyst such as, for example, platinum.

Other curing agents/catalysts available for use in such two component systems are tempered steel, heat, crosslinkers, gamma radiation, and ureaformaldehyde.

As described above, it will be noted that this two component system is a non-solvent system. That is, the two components react together in the presence of salt, which is compounded with the two component system as described below. The two components are not a polymer and a solvent.

Once an appropriate two component polymer system has been chosen, it is compounded with a water soluble inorganic salt such as, but not confined to, sodium chloride. The size and shape of the pores 16 of the honeycomb network are dictated by the choice of the specific inorganic salt that is compounded with the polymer system. Typically, the crystals of salt chosen are ground and then put through a sieve whose chosen mesh size corresponds to the size requirement for the pore diameter to be utilized in the graft 10. The salt crystals are then placed in a drying oven at 135° C. for a period of no less than 24 hours.

The polymer system is then processed according to the method recommended by the manufacturer of the particular polymer system utilized and the dried salt crystals are mixed with the polymer system and compounded. The porosity and flexibility of the graft 10 is dependent upon the ratio of water soluble inorganic salt to the polymer system with this ratio ranging anywhere from 25-755 by weight.

Once compounded, the water soluble inorganic salt and polymer are injection molded or reaction injection molded to form a tube of known inner and outer diameter. If desired, the tube can be extruded. Once the salt filled polymer tubes are formed, they are leached in water, dissolving the salt crystals and leaving a porous network of interconnecting cells 16 as illustrated in FIG. 3.

This method of formation provides for the rapid and reproducible formation of simple geometries within thin walled grafts as well as large, intricate geometries within thick walled grafts as dictated by the location in which the graft is to be utilized. In use, the cardiovascular graft formed by the method defined above is sutured into position to bypass a stenotic region of a blood vessel for replacing the naturally occurring blood vessel.

Although the graft 10 of the present invention as defined above is predominantly used as a cardiovascular graft, the graft 20 may also be used alternatively as a sewing collar for the fixation of a pervenous lead to muscle proximally underlying an area of entry of a lead into a blood vessel. Further, the graft 10 may be used as a portion of the insulating material on any pacing lead to provide an area of tissue ingrowth capability to the lead for purposes of fixing the lead in place. Still further, the graft 10 may be used as a filter to prevent blockage of catheters by cellular or proteinaceous debris.

It will be apparent form the foregoing description that the graft 10 and method for formation of the graft 10 described above have a number of advantages, some of which have been describe above and others of which are inherent in the invention. For example, the use of a non-solvent method in the formation of the graft prevents possible physiological reactions of tissue to any solvent that might not be leached from the polymer in the final steps of forming grafts with a solvent system. Further, by reaction injection or injection molding, there is no limit to the wall thickness which can be obtained by the present method.

Also, modifications can be made to the graft and method of the present invention without departing from the teachings of the present invention. Accordingly, the scope of the invention is only to be limited as necessitated by the accompanying claims.

I claim:

1. A method for forming a biocompatible polymer graft particularly adapted for cardiovascular use, said method comprising the steps of: choosing a suitable, nonsolvent, two component, hydrophobic biocompatible polymer system from which the graft may be formed; choosing suitable water soluble inorganic salt crystals to be compounded with the biocompatible polymer system; grinding the salt crystals and passing same through a sieve having a predetermined mesh size; drying the salt crystals; compounding the salt crystals with the biocompatible polymer system; forming a tube from said compounded salt and polymer system by reaction injection or cast molding; and leaching the salt crystals from the formed tube with water, said leaching of said salt crystals providing a tube with a network of interconnecting cells formed in the area from which the salt crystals have been leached.

2. The method of claim 1 wherein the biocompatible polymer system comprises a polymer resin and curing agent.

3. The method of claim 2 wherein said polymer is chosen from the group comprising polyurethane, silicone rubber and polytetrafluoroethylene.

4. The method of claim 2 wherein said curing agent is chosen from the group comprising platinum, tempered steel heat, cross-linkers, gamma radiation and ureaformaldehyde.

5. The method of claim 1 wherein said inorganic salt crystals are sized to provide cells of predetermined size.

6. The method of claim 5 wherein said inorganic salt are sodium chloride crystals.

7. The method of claim 1 wherein said inorganic salt crystals are dried crystals which have been dried in an oven at a temperature between 100° and 175° C. for a minimum of twenty-four hours.

8. The method of claim 7 wherein said temperature is approximately 135° C.

9. The method of claim 1 wherein the ratio of water soluble inorganic salt crystals to said biocompatible polymer system is between approximately 25% and 75% by weight.

10. The method of claim 9 wherein said range is determined by the required flexibility and/or porosity of the graft to be fabricated.

11. The method of claim 1 wherein said cells are of a uniform diameter within the graft.

12. The method of claim 11 wherein the diameter of the cells in the graft is between approximately 10 and 200 microns.

13. The method of claim 1 wherein the wall thickness of the graft is between approximately 0.5 cm and 4 cm depending on the location at which the graft is to be used in the cardiovascular system.

14. A graft made by the process of claim 1.

* * * * *